(12) United States Patent
Molla et al.

(10) Patent No.: US 10,677,775 B2
(45) Date of Patent: Jun. 9, 2020

(54) MICROFLUIDIC METHOD FOR DETECTION OF FINES, WAXES, AND ASPHALTENES IN OIL

(71) Applicant: SCHLUMBERGER TECHNOLOGY CORPORATION, Sugar Land, TX (US)

(72) Inventors: Shahnawaz H. Molla, Watertown, MA (US); Vincent Sieben, Auburndale, MA (US); Farshid Mostowfi, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 225 days.

(21) Appl. No.: 15/739,831

(22) PCT Filed: Jun. 26, 2015

(86) PCT No.: PCT/US2015/037896
§ 371 (c)(1),
(2) Date: Dec. 26, 2017

(87) PCT Pub. No.: WO2016/209248
PCT Pub. Date: Dec. 29, 2016

(65) Prior Publication Data
US 2019/0011423 A1    Jan. 10, 2019

(51) Int. Cl.
*G01N 33/28* (2006.01)
*G01N 15/06* (2006.01)
*G01N 21/31* (2006.01)
*B01L 3/00* (2006.01)
*G01N 11/08* (2006.01)

(52) U.S. Cl.
CPC .... *G01N 33/2823* (2013.01); *B01L 3/502753* (2013.01); *G01N 15/0618* (2013.01);
(Continued)

(58) Field of Classification Search
CPC ............ G01N 33/2823; G01N 33/2835; B01L 3/502753
See application file for complete search history.

(56) References Cited

U.S. PATENT DOCUMENTS 4,023,397 A * 5/1977 Ouvrard ................. G01N 11/08
374/24
5,454,257 A * 10/1995 Per ..................... G01N 33/2835
374/16

(Continued)

FOREIGN PATENT DOCUMENTS

WO    2013126732 A1    8/2013
WO    2015023343 A1    2/2015

OTHER PUBLICATIONS

ASTM D6560, "Standard Test Method for Determination of Asphaltenes (Heptane Insolubles) in Crude Petroleum and Petroleum Products", 2017, 6 pages.

(Continued)

*Primary Examiner* — John Fitzgerald

(57) ABSTRACT

A method of characterizing an oil sample includes: flowing a first sample containing an oil through a microfluidic device that has a microfluidic filter while controlling the temperature of the first sample such that it is above wax appearance temperature for the oil and measuring and analyzing pressure difference across the filter over time to detect the presence of fines in the oil. The method further includes: flowing a second sample containing the oil through the microfluidic device while controlling the temperature of the second sample such that the temperature of the second sample is lower than wax appearance temperature for the oil and measuring and analyzing pressure difference across the filter over time as the second sample is filtered to detect the presence of wax in the oil.

15 Claims, 10 Drawing Sheets

(52) U.S. Cl.
CPC ......... *G01N 21/31* (2013.01); *G01N 33/2835* (2013.01); *B01L 2300/0627* (2013.01); *B01L 2300/0681* (2013.01); *B01L 2300/18* (2013.01); *G01N 11/08* (2013.01)

(56) References Cited

U.S. PATENT DOCUMENTS

| | | |
|---|---|---|
| 8,269,961 B2 | 9/2012 | Mostowfi et al. |
| 8,797,517 B2 | 8/2014 | Karnes et al. |
| 9,068,962 B2 * | 6/2015 | Schneider .............. G01N 31/16 |
| 9,278,351 B2 * | 3/2016 | Mostowfi ........... G01N 33/2823 |
| 9,346,049 B2 * | 5/2016 | Mostowfi ........... G01N 33/2823 |
| 10,031,122 B2 * | 7/2018 | Sieben ..................... G01N 1/28 |
| 2010/0192679 A1 * | 8/2010 | Brown ............... G01N 15/0272 73/61.78 |
| 2010/0266450 A1 * | 10/2010 | Wimberger-Friedl ....................... B01L 3/5023 422/68.1 |
| 2014/0369889 A1 * | 12/2014 | Mostowfi ........... G01N 33/2823 422/82.09 |
| 2014/0375991 A1 * | 12/2014 | Schneider .............. G01N 31/16 356/326 |
| 2015/0209781 A1 * | 7/2015 | Mostowfi ........... G01N 33/2823 422/503 |
| 2015/0209782 A1 * | 7/2015 | Mostowfi ........... G01N 33/2823 422/503 |
| 2016/0097757 A1 * | 4/2016 | Sieben ..................... G01N 1/28 436/60 |
| 2016/0208601 A1 * | 7/2016 | Molla ..................... E21B 37/00 |

OTHER PUBLICATIONS

Nguyen, N-T. et al., "Micromixers—a review", Journal of Micromechanics and Microengineering, 2005, 15, pp. R1-R16.

Roenningsen et al., "Wax Precipitation from North Sea Crude Oils: 1. Crystallization and Dissolution Temperatures, and Newtonian and Non-Newtonian Flow Properties", Energy & Fuels, 1991, 5(6), pp. 895-908.

* cited by examiner

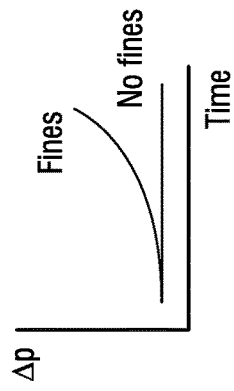
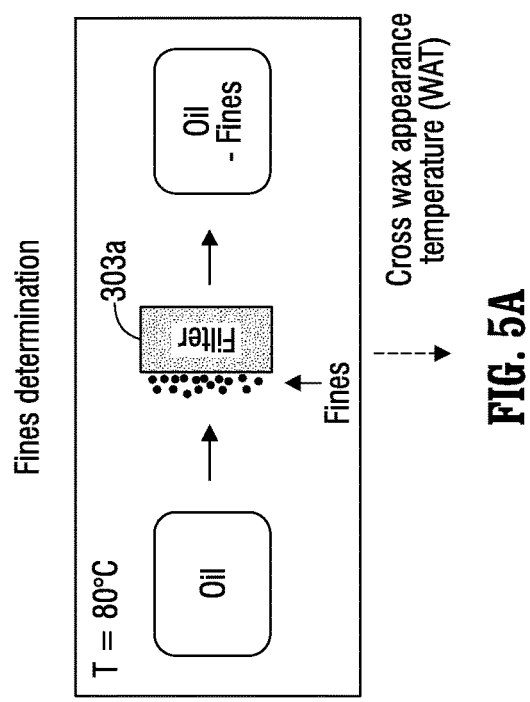
FIG. 5A
FIG. 5B
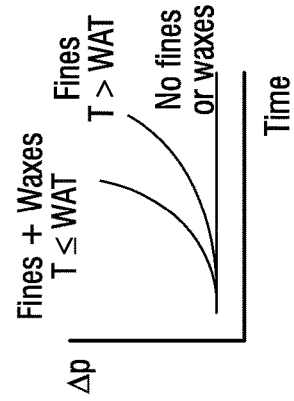
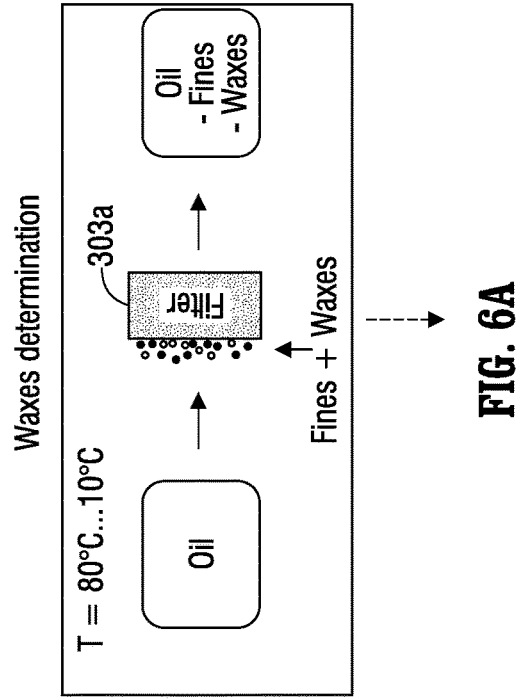
FIG. 6A
FIG. 6B

MICROFLUIDIC METHOD FOR DETECTION OF FINES, WAXES, AND ASPHALTENES IN OIL

BACKGROUND

Field

The present description relates to oil analysis and more particularly, to analysis of fines, waxes, and asphaltenes in oil.

Description of Related Art

Oil, and in particular, crude oil, may be composed of multiple constituents including fines, waxes, and asphaltenes. Fines are composed of clay minerals such as kaolinite, smectite, illite, chlorite, silicates, carbonates, etc., metals, and other formation particles not soluble in organic solvents like toluene or heptane. Crude oils also contain paraffin waxes that are soluble in the oil liquid phase at reservoir conditions. Such waxes are typically comprised of long-chain hydrocarbons (n-paraffins) with carbon chain lengths ranging from C17 to C90+. When the crude oil temperature drops, the high molecular weight paraffins become less soluble in the liquid and dissolved wax molecules tend to crystallize and form solid particles. Asphaltenes are the most polar components in crude oil and are defined by their solubility; e.g., asphaltenes are completely soluble in toluene and insoluble in heptane (ASTM D6560, 2005). These aggregates precipitate upon composition changes to the oil or induced pressure and temperature variations during production.

Determining the presence of fines, waxes, and asphaltenes within an oil sample are important measurements for both upstream and downstream operations. When oil is transported from the reservoir to surface facilities, variations in temperature, variations in pressure, and modifications to composition may cause solid molecules to precipitate out of the liquid phase and deposit as solids on internal surfaces of reservoirs, pipes, separators, and other equipment. The deposits reduce the cross-sectional area of crude oil flow paths and can interrupt and potentially halt production by restricting flow. Therefore, it is important to flag the existence of inorganic or organic content that may precipitate to ensure optimal flow assurance and to prevent adverse deposition. Fines, waxes, and asphaltenes and combinations thereof can form complex deposits. Selection of prevention and remediation strategies requires composition knowledge so that the source of the deposit can be appropriately managed.

SUMMARY

In this disclosure, methods and apparatuses are described for determining the presence of fines, waxes, and asphaltenes in oil. One method employs transmembrane pressure measurements of a sample containing oil that flows through a microfluidic filter while the temperature of the sample is regulated.

According to one aspect, a method of characterizing an oil sample includes: i) flowing at least one sample containing an oil through a microfluidic device that has a microfluidic filter while controlling the temperature of the sample flowing through the microfluidic device such that the temperature of the sample is above wax appearance temperature for the oil; ii) in conjunction with i), using the microfluidic filter to perform microfluidic filtering operations that selectively block fines contained in the oil from passing through the microfluidic filter; iii) in conjunction with i) and ii), measuring and analyzing pressure difference across the microfluidic filter over time as the sample is filtered in order to detect the presence of fines in the oil; iv) flowing at least one other sample containing the oil through the microfluidic device while controlling the temperature of the sample flowing through the microfluidic device such that the temperature of the sample is lower than the wax appearance temperature for the oil; v) in conjunction with iv), using the microfluidic filter to perform microfluidic filtering operations that selectively block at least one of wax that crystallizes from the oil and fines contained in the oil from passing through the microfluidic filter; and vi) in conjunction with iv) and v), measuring and analyzing pressure difference across the microfluidic filter over time as the sample is filtered in order to detect the presence of wax in the oil.

The method may also include using a microfluidic mixer that is part of the microfluidic device to perform microfluidic mixing operations that mix a solvent with oil upstream of the microfluidic mixer. The mixing of the solvent with the oil can be used to improve the flowability of viscous oil in the microfluidic device.

The method may also include vii) flowing at least one other sample containing the oil through the microfluidic device while controlling the temperature of the sample flowing through the microfluidic device such that temperature of the sample is below wax appearance temperature for the oil; viii) in conjunction with vii), using a microfluidic mixer that is part of the microfluidic device to perform microfluidic mixing operations that mix an asphaltene precipitant and/or solvent with the oil upstream of the microfluidic filter; ix) in conjunction with vii) and viii), using the microfluidic filter of the microfluidic device to perform microfluidic filtering operations that selectively block asphaltenes that precipitate from the mixture of viii) from passing through the microfluidic filter; and x) in conjunction with vii), viii), and ix), measuring and analyzing pressure difference across the microfluidic filter over time as the mixture is filtered in order to characterize asphaltenes in the oil.

BRIEF DESCRIPTION OF THE DRAWINGS

FIG. 5A is a schematic illustration of the automated test apparatus shown in FIG. 1 showing fines filtration.

FIG. 5B is a graph showing transmembrane pressure differential as a function of time during fines filtration.

FIG. 6A is a schematic illustration of the automated test apparatus shown in FIG. 1 showing wax formation.

FIG. 6B is a graph showing transmembrane pressure differential as a function of time during wax formation.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As used herein, the term "microfluidics" or "microfluidic" refers to a device, apparatus or system that deals with the behavior, precise control and manipulation of fluids that are geometrically constrained to a small, typically sub-millimeter, scale. The device, apparatus, or system can employ small, typically sub-millimeter, scale channels that are etched into planar substrates, such as glass, metal, sapphire, plastics, and ceramics, where networks of these embedded channels transport the sample from one operation to the next. The manipulation of small volumes of fluid enables precise control of reagents and seamless automation of several consecutive steps.

One aspect of the disclosure relates to the determination of fines, waxes, and asphaltenes in an oil sample.

Figure 1:
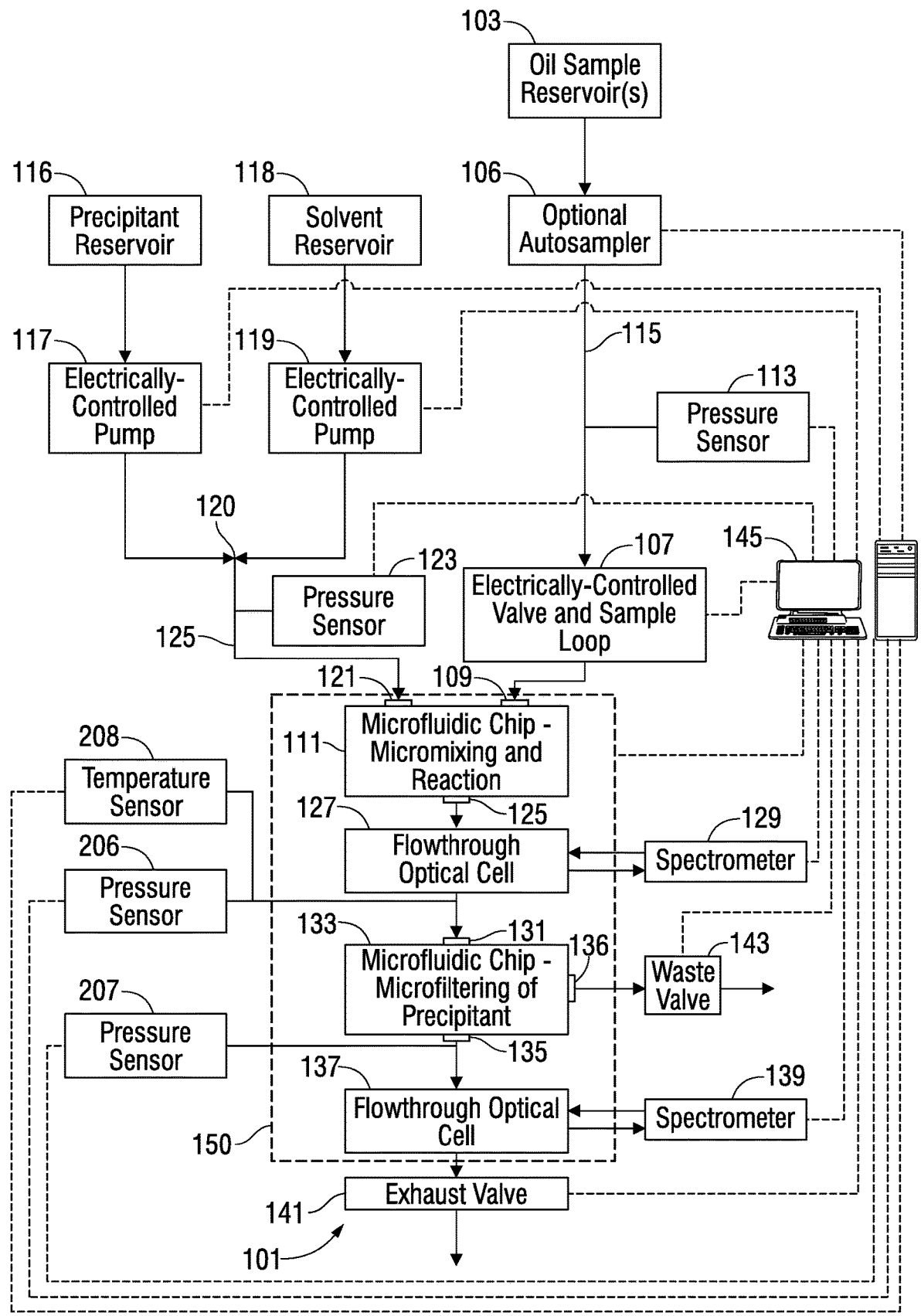
FIG. 1 is a block diagram of an automated test apparatus configured to characterize fines, waxes, and asphaltenes in an oil in accordance with the present disclosure.

FIG. 1 depicts an illustrative embodiment of an apparatus 101 for automated fluid analysis of an oil sample. The apparatus 101 includes a sample reservoir 103 that holds an oil sample and an optional autosampler 106 that is fluidly coupled between the sample reservoir 103 and an electrically-controlled valve and sample loop 107 with a defined volume. Optionally, a syringe can be used in place of the autosampler 106 and the sample reservoir 103 may be a reservoir of the syringe. The oil sample can include lighter (more volatile) molecular weight oil components as well as heavy (less volatile) molecular weight components such as heavy oil and bitumen. The autosampler 106 can be operated to inject a defined volumetric slug of the oil sample held by the sample reservoir 103 into the defined volume of the sample loop 107. Alternatively, a defined volumetric slug of the oil sample held by the sample reservoir 103 can be injected manually with the syringe into the defined volume of the sample loop 107. The defined volumetric slug of the oil sample loaded into the sample loop 107 flows (for example, at or near a desired flow rate) into an inlet 109 of a microfluidic chip 111. A pressure sensor 113 can be disposed within a flow line 115 between the autosampler 106 and the valve 107 in order to monitor the fluid pressure of the sample supplied to the inlet 109. The pressure sensor 113 can be used as a form of feedback for the stability of the flow of the defined volumetric slug of the oil sample into the inlet 109. The sample reservoir 103 can be embodied as an electrically-controlled syringe pump, such as the Mitos Duo XS-Pump available from The Dolomite Center Limited of Royston, United Kingdon, where the syringe of the pump acts as the sample reservoir 103 that stores the oil sample.

The reservoir 103 may include a heater and/or a chiller and a temperature sensor that can be configured to thermostatically control the temperature of the oil in the reservoir 103. In one embodiment, the temperature of the oil may be maintained at a temperature within the range of 10° C. to 80° C.

The apparatus 101 also includes a reservoir 116 and an electrically-controlled pump 117 that is fluidly coupled to the reservoir 116. The reservoir 116 holds a fluid (referred to herein as a "precipitant") that causes asphaltenes to precipitate from an oil sample when present. The precipitant can be an n-alkane (such as n-heptane ($C_7H_{16}$), n-hexane ($C_6H_{14}$), or n-pentane ($C_5H_{12}$) or other solvents, such as petroleum ether, ethyl acetate, alcohols or any other solvent which can cause asphaltene precipitation due to a limited solubility.

The precipitant reservoir 116 may include a heater and/or a chiller and a temperature sensor that can be configured to thermostatically control the temperature of the precipitant in the reservoir 116. In one embodiment, the temperature of the precipitant may be maintained at a temperature within the range of 10° C. to 80° C.

The apparatus 101 also includes a reservoir 118 and an electrically-controlled pump 119 that is fluidly coupled to the reservoir 118. The reservoir 118 holds a fluid (referred to herein as a "solvent") that dissolves asphaltene solids when present in an oil sample. The solvent can be toluene, dichloromethane (DCM), xylene, benzene, methyl naphthalene, cyclohexane, tetrahydrofuran (THF), chloroform, trichloroethylene, tetrachloroethylene, carbon tetrachloride, carbon disulfide, or any other solvent that dissolves asphaltenes.

The solvent reservoir 118 may include a heater and/or a chiller and a temperature sensor that can be configured to thermostatically control the temperature of the solvent in the reservoir 118. In one embodiment, the temperature of the solvent may be maintained at a temperature within the range of 10° C. to 80° C.

The outputs of the pumps 117, 119 merge at T-section 120 that combines the output of the two pumps 117, 119. In an alternate configuration, a two-port microfluidic mixer chip can be used instead of the T-section 120 in order to combine the output of the two pumps 117, 119. The pumps 117, 119 are operated to inject the precipitant alone, the solvent alone or a mixture of a controlled ratio of the precipitant and the solvent into an inlet port 121 of microfluidic chip 111. A pressure sensor 123 can be disposed within the flow line 125 between the T-section 120 and the inlet port 121 in order to monitor the pressure of the pumps 117, 119. Such pump pressure can be used as a form of feedback to adjust the operation of the pumps 117, 119 in order to maintain pressure levels within the pressure rating of the apparatus 101 and to ensure that the flow of the precipitant alone, the solvent alone, or the controlled ratio of the precipitant and the solvent into the inlet port 121 occurs as desired. Thus, the pressure sensor 123 can be used as a form of feedback for the stability of the flow into the inlet port 121. The pressure sensor 123 can also be used to detect an overpressure of apparatus 101, such as may result from excessive asphaltene build up, so that the operation of the apparatus 101 can be halted. The pumps 117, 119 can be electrically-controlled syringe pumps, such as the Mitos Duo XS-Pump, where the syringe of the respective syringe pumps acts as the reservoirs 116, 118 that hold an amount of the precipitant and the solvent, respectively.

Figure 2:
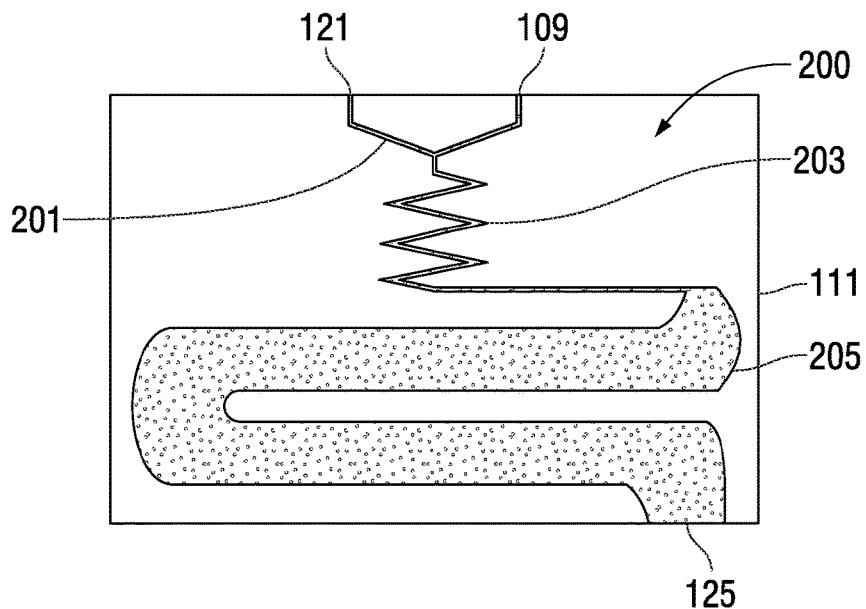
FIG. 2 is a schematic representation of one embodiment of the microfluidic chip 111 of FIG. 1.

With temporary reference to FIG. 2, the microfluidic chip 111 includes an internal mixer section 200 that provides microfluidic mixing of the fluids introduced into the inlet ports 121 and 109, as well as an internal reactor section 205 that provides a microfluidic flowpath that allows for microfluidic processes where solid asphaltene content (typically referred to as asphaltene floccules or asphaltene flocks) may precipitate from the mixture generated by the mixer section. Of course, it is possible for the oil sample to pass through the internal reactor section 205 without mixing with any solvent or precipitant, such as when solvent and precipitant are not pumped into the chip 111 and when neat oil is being analyzed.

In the case when the oil and precipitant are pumped into the microfluidic chip 111, when the oil mixes and reacts with precipitant the precipitated asphaltene flock is carried as a suspension in the liquid phase content of the mixture. The liquid phase content of the mixture includes the maltenes of the oil sample, which are the lower molecular weight components of the oil sample that remain after removing the precipitated asphaltene content. The maltenes are also soluble in the precipitant.

The microfluidic chip 111 also includes an outlet port 125 at the downstream end of the internal reactor section 205 flow path. The outlet port 125 of the microfluidic chip 111 is fluidly coupled to the inlet of a flowthrough optical cell 127. A spectrometer 129 is optically coupled to the flowthrough optical cell 127 and can be operated to derive an optical spectrum of whatever fluids (neat oil or mixtures of oil and solvent and/or precipitant) flow from the outlet port 125 of the microfluidic chip 111 and through the flowthrough optical cell 127.

The outlet of the flowthrough optical cell 127 is fluidly coupled to an inlet port 131 of a microfluidic chip 133. A pressure sensor 206 and a temperature sensor 208 are also fluidly coupled to the inlet port 131. The pressure sensor 206 and the temperature sensor 208 are configured to measure the pressure and temperature, respectively, of the fluid that flows out of the optical cell 127 and into the microfluidic chip 133. The inlet port 131 is fluidly coupled to an internal filter section that provides microfluidic filtering that is configured to trap solid phase hydrocarbon components (i.e., fines, waxes, and/or asphaltene flock) while passing the remaining soluble liquid phase hydrocarbon components that are not filtered to an outlet port 135. Note that an increase in the pressure measured by the pressure sensor 206 can be used to indicate an increase in the amount of solid material filtered and accumulated by the filter section 303 (i.e., the amount of clogging of the filter section 303), which information can be used as a form of feedback to indicate the formation of fines, waxes, and asphaltenes, as described in greater detail below. The internal filter section 303 of the microfluidic chip 133 is also fluidly coupled to a waste port 136 that allows for flushing and removal of the solid phase hydrocarbon components (i.e., the asphaltene flock) that is trapped by the internal filter section of the microfluidic chip 133.

The outlet port 135 of the microfluidic chip 133 is fluidly coupled to the inlet of a flowthrough optical cell 137. A pressure sensor 207 is also fluidly coupled to the outlet port 135. The pressure sensor 207 is configured to measure the pressure of the fluid that flows out of the microfluidic chip 133 and into the optical cell 137. The pressure measured by the pressure sensor 207, along with the pressure measured by the pressure sensor 206, can be used as a form of feedback to indicate the formation of fines, waxes, and asphaltenes, as described in greater detail below.

A spectrometer 139 is optically coupled to the flowthrough optical cell 137 and can be operated to derive an optical spectrum of fluid that flows from the outlet 135 of the microfluidic chip 133 and through the flowthrough optical cell 137. An electrically-controlled exhaust valve 141 can be fluidly coupled to the outlet of the flowthrough optical cell 137. An electrically-controlled waste valve 143 can be fluidly coupled to the waste port 136 of the microfluidic chip 133.

The microfluidic chips 111 and 133 may be configured so that the fluids flowing through those chips 111 and 133 can be temperature controlled (heated and cooled) and regulated based on the temperature measured by temperature sensor 208. In one embodiment, the microfluidic chips 111 and 133 are thermally coupled to a temperature-controlled surface 150 in thermal communication with the chips 111 and 133. The temperature-controlled surface 150 may be maintained at a temperature in a range between 10° C. and 80° C. so that the temperature of the fluid flowing through chips 111 and 133 can be controlled. The temperature measured by the temperature sensor 208 may be used as a feedback for control of the temperature-controlled surface 150. For example, as described in greater detail below, the temperature of temperature-controlled surface 150 may be adjusted downward to adjust the temperature of the fluid flowing through the chips 111 and 133 during a workflow, described in greater detail below with reference to FIG. 4.

FIG. 2 is a schematic view of one embodiment of the microfluidic chip 111 of FIG. 1, which includes two inlet ports 109 and 121 and a passive internal mixer section 200 that is fluidly coupled to the two inlet ports 109, 121. The passive internal mixer section 200 includes a y-type junction part 201 that leads from the two inlet ports 109, 121 to a mixing part 203. The passive internal mixer section 200 provides microfluidic mixing of the fluids introduced into the inlet ports 109, 121. The mixing part 203 can employ chaotic split and recombine microfluidic mixing techniques or other suitable microfluidic techniques as described in Nguyen, N-T and Wu, Z., "Micromixers—a Review," *Journal of Micromechanics and Microengineering* 15, no. 2 (2005): R1, herein incorporated by reference in its entirety. The downstream end of the mixing part 203 extends to an internal reactor section 205 that is realized by a serpentine path that has larger cross-sectional diameter as compared to the channel(s) of the mixing part 203 as is evident from FIG. 2. The internal reactor section 205 allows for precipitation of asphaltenes from the mixture generated by the mixing part 203 in a case where the oil is mixed with precipitant. Any asphaltene flock is carried as a suspension in the liquid phase of the mixture. Otherwise, if the oil is introduced to the internal reactor section 205 neat or is diluted with solvent and no precipitant is mixed, asphaltenes are not expected to precipitate out of the oil. The downstream end of the larger diameter serpentine path of the internal reactor section 205 terminates at the outlet port 125. Note that the smaller dimensions of the mixing part 203 enable more effective and rapid mixing because of shorter diffusion distances and the larger dimensions of the internal reactor section 205 allow asphaltene flocculates to grow to a significant size for capture by the filter section 303 as described below.

Figure 3:
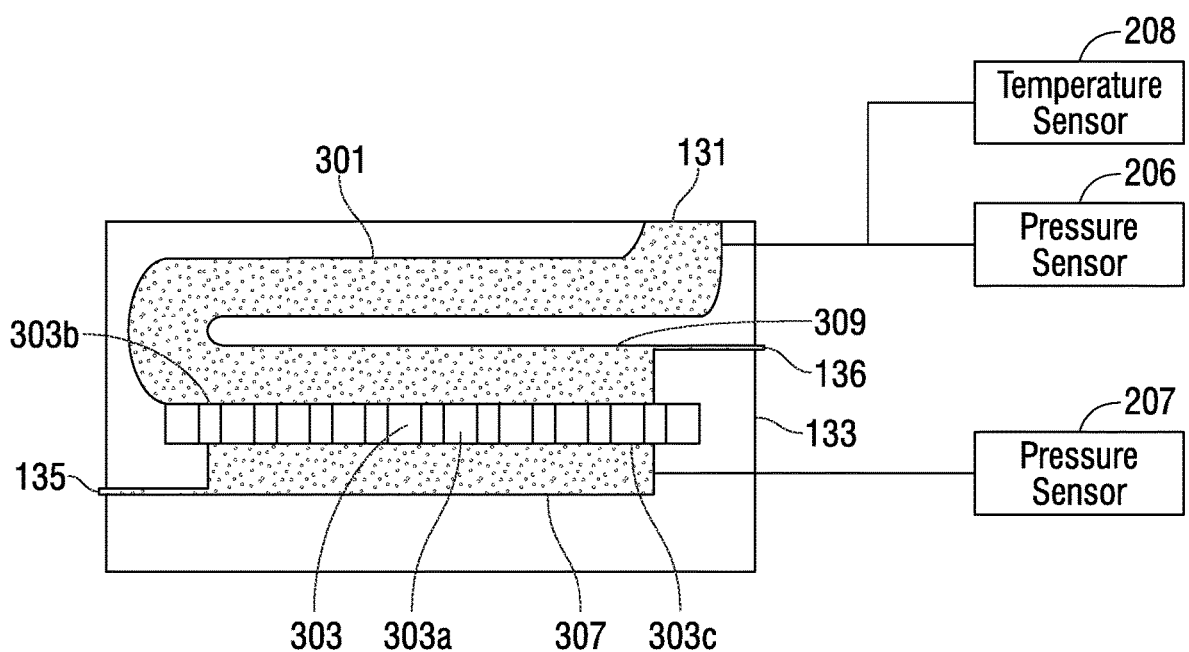
FIG. 3 is a schematic representation of one embodiment of the microfluidic chip 133 of FIG. 1.

FIG. 3 is a schematic view of one embodiment of the microfluidic chip 133 of FIG. 1, which includes an inlet port 131 and an inlet flowpath 301 that leads to a filter section 303. The filter section 303 includes a membrane filter 303a providing microfluidic filtering to trap solid phase components (such as fines, waxes, and asphaltenes) while allowing the remaining soluble components of the sample to pass to an outlet flowpath 307 (on a bottom side 303c of the membrane filter 303a) that leads to the outlet port 135. The inlet 303b of the membrane filter 303a (disposed on its top side) includes a waste flowpath 309 that leads to the waste port 136. The waste flowpath 309 and the waste port 136 allow for flushing and removal of the solid phase components that are trapped by the membrane filter 303a of the filter section 303 of the microfluidic chip 133.

In one embodiment, the flowthrough optical cells 127, 137 can be realized by an optical absorbance flow cell, such as the FIAlab SMA-Z-2.5 cell with fused silica windows and a 2.5 mm optical path and a 2.0 µl internal volume available from FIAlab Instruments, Inc. of Bellevue, Wash., USA. Custom flow cells that are either machined in the chip holders or integrated directly on the chip can also be used. The spectrometers 129, 139 can be realized by a broadband spectrometer, such as the model HR2000+ available from OceanOptics, Inc. of Dunedin, Fla., USA. The broadband spectrometer can be used in conjunction with a broadband light source which can be based on a tungsten filament bulb (such as the model LS-1 light source available from Ocean-Optics, Inc.). Fiber optic waveguides can be used to optically couple the optical absorbance flow cell to both the broadband light source and the broadband spectrometer.

A computer processing system 145 can be programmed with suitable control logic that interfaces to the electrically-controlled pumps 117 and 119 via wired or wireless signal paths therebetween, that interfaces to the electrically-controlled valves 107, 141, and 143 via wired or wireless signal paths therebetween, that interfaces to the temperature-controlled surface 150 via wired or wireless signal paths therebetween, that interfaces to the optional autosampler 106 via wired or wireless signal paths therebetween, that interfaces to the pressure sensors 113, 123, 206, and 207 via wired or wireless signal paths therebetween, and that interfaces to the temperature sensor 208 via wired or wireless signal paths therebetween. The computer processing system 145 can also interface to the spectrometers 129, 139 via wired or wireless signal paths therebetween. The control logic of the computer processing system 145 (which can be embodied in software that is loaded from persistent memory and executed in the computing platform of the computer processing system 145) is configured to control the different parts of the apparatus 101 to carry out an automated sequence of operations (workflow) that characterizes the solubility profile of an oil sample. The control logic can be configured by a testing script, which is input into and executed by the computer processing system 145 to perform automatic control operations as specified by the testing script. The computer processing system 145 can include a graphical user interface that allows the user to specify the sequence of automatic control operations and/or the parameters (such as pressures, flow rates, temperatures, etc.) for such automatic control operations.

A workflow for detecting the presence of fines, waxes, and asphaltenes in an oil sample will now be described with reference to FIGS. 4A and 4B.

At 401 an oil sample in the reservoir 103, along with the microfluidic chips 111 and 133, are heated to an upper temperature sufficient so that all of the wax in the oil sample will remain dissolved in the oil. In other words, the temperature is set above the wax appearance temperature (WAT) of the oil sample.

At 402, the oil in the reservoir 103 (as heated in 401) is introduced into microfluidic chip 111 through inlet port 109. While the use of neat oil (oil that has not been mixed with solvent from reservoir 118) is preferred, oils with high viscosity (>500 cP) or high fines/wax content may need to be diluted with solvent from the solvent reservoir 118 to comply with instrumentation specifications/limits. Therefore, if the viscosity of the oil is too high to flow through the microfluidic chips 111 and 133, solvent from reservoir 118 may also be injected through inlet 121 into microfluidic chip 111. The syringe (sample reservoir) 103 is used alone to push the sample from the manually loaded sample loop 107 to the microfluidic reactor chip 111. The heated oil sample (whether neat or diluted) passes through the reactor chip 111 and the first optical cell 127. The oil sample proceeds to the microfluidic filtration chip 133 that is coupled to the membrane filter 303a, which may have an average pore size of 200 nm or smaller, under applied pressure.

At 403, the pressure measurements of pressure sensors 206 and 207 are recorded over time while the heated oil flows through the microfluidic chips 111 and 133.

At 404, changes in the transmembrane pressure differential over time (the pressure differential across the membrane filter 303a as recorded in 403 over time) are calculated. The time span of interest may be from the beginning of the introduction of the sample to a time (referred to herein as the "peak arrival time") where the measured transmembrane pressure differential saturates at the maximum differential pressure measurable by the pressure sensors 206 and 207, or the beginning of the introduction of the sample to some predefined time offset thereafter, or some other suitable time interval.

At 405, the changes in transmembrane pressure differential over time as calculated in 404 are analyzed to determine the presence of fines in the oil sample. Such fines accumulate on the upstream side of the membrane filter 303a as shown schematically in FIG. 5A. In one embodiment, such an analysis may include determining an average slope of the transmembrane pressure differential over the time span of interest and comparing the average slope to a predefined threshold, such as zero. If the average slope of the transmembrane pressure differential over the time span of interest is greater than zero (i.e., is a positive value), then this condition can indicate the presence of fines in the oil sample. However, if the average slope of the transmembrane pressure differential over the time span of interest is not greater than zero, then this condition can indicate that fines are not present in the oil sample. For example, consider the plots of the change in transmembrane pressure differential ($\Delta p$) over time shown in FIG. 5B. The steep line of FIG. 5B indicates that the transmembrane pressure differential increases over the time span, which can indicate the presence of fines in the oil sample. On the other hand, the flat line in FIG. 5B indicates that the transmembrane pressure differential remains substantially unchanged over the time span, which can indicate the lack of fines in the oil sample. Due to measurement limitations and noise in measurements, instead of comparing the slope of the transmembrane pressure differential to a value of zero, the slope may be compared to a non-zero threshold, exceeding which would be indicative of a rise in differential pressure as opposed to merely noise in the measurement of transmembrane pressure differential.

If the analysis in 406 indicates that fines are present in the oil sample, then the detection of fines is set to 'true' in 408. However, if the analysis in 406 indicates that fines are not present in the oil sample, then the detection of fines is set to 'false' in 407.

Figure 4A:
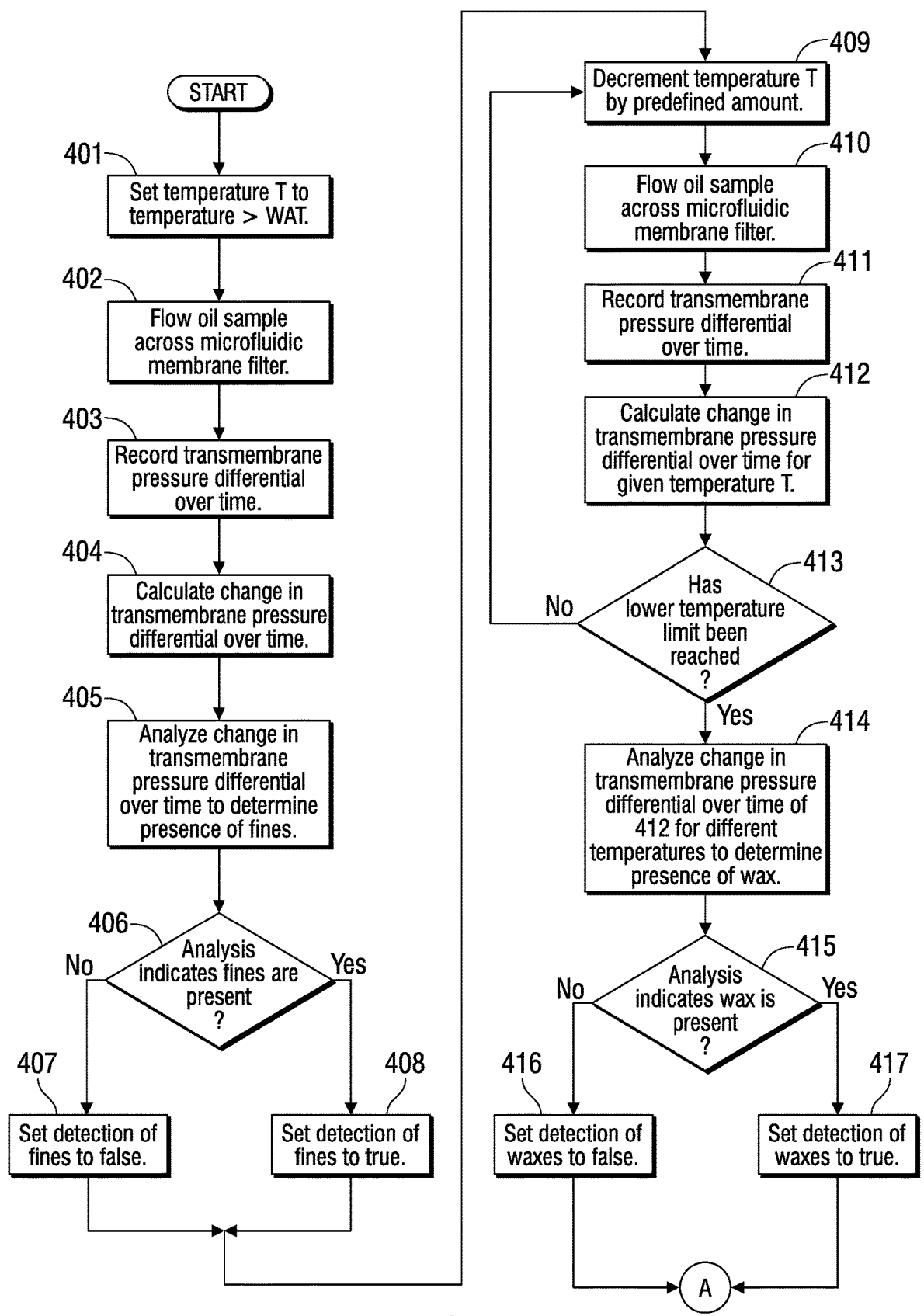
FIGS. 4A and 4B are flowcharts that illustrate an embodiment of a workflow for characterizing fines, waxes, and asphaltenes in an oil in accordance with an aspect of the disclosure.
Figure 4B:
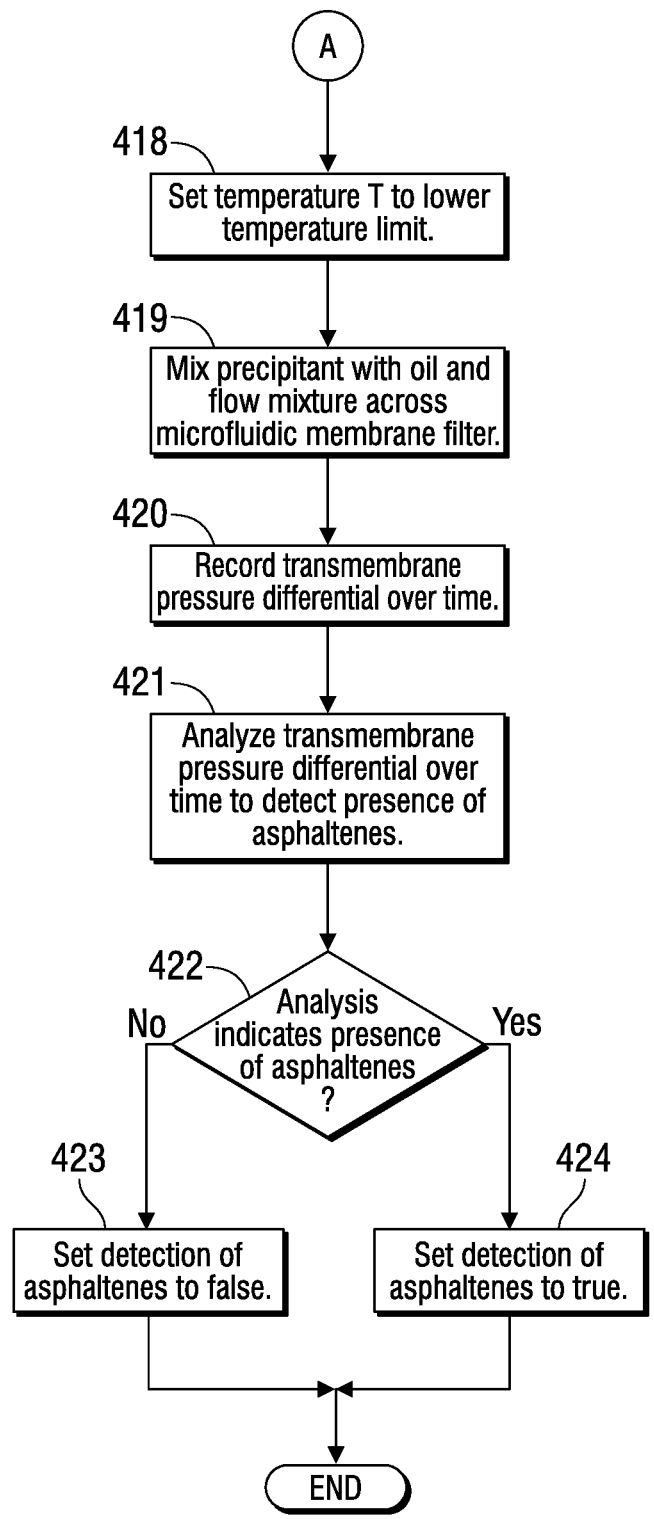

After the fines detection portion of the workflow of FIGS. 4A and 4B has been performed in 401 to 408, the wax detection portion of the workflow begins, wherein the temperature of the oil sample is decremented by pre-determined steps while the transmembrane differential pressure is measured and analyzed for detecting the presence of wax in the oil sample. The steps in temperature can be configured to begin at a temperature above WAT for the oil sample and end at a lower temperature limit below WAT for the oil sample.

At 409, the temperature of the oil sample in the reservoir 103, along with the temperature of microfluidic chips 111 and 133 is decremented from the current temperature (which is initially above WAT for the oil sample) by a predefined amount. For example, the temperature of the reservoir 103 and the temperature of the temperature-controlled surface 150 can be decremented so that the oil temperature measured by temperature sensor 208 is at the set temperature.

At 410, the oil in the reservoir 103 (as heated in 409) is introduced into microfluidic chip 111 through inlet port 109. While the use of neat oil (oil that has not been mixed with solvent from reservoir 118) is preferred, oils with high viscosity (>500 cP) or high fines/wax content may need to be diluted with solvent from the solvent reservoir 118 to comply with instrumentation specifications/limits. Therefore, if the viscosity of the oil is too high to flow through the microfluidic chips 111 and 133, solvent from reservoir 118 may also be injected through inlet 121 into microfluidic chip 111. The syringe 103 is used alone to push the sample from the manually loaded sample loop 107 to the microfluidic reactor chip 111. The heated oil sample (whether neat or diluted) passes through the reactor chip 111 and the first optical cell 127. The oil sample proceeds under applied pressure to the filtration chip 133 that is coupled to the membrane filter 303a.

At 411, the differential pressure measurements of pressure sensors 206 and 207 are recorded over time while the heated oil flows through the microfluidic chips 111 and 133.

At 412, changes in the transmembrane pressure differential over time (the pressure differential across the membrane filter 303a as recorded in 411 over time) are calculated for the respective decremented temperature. The time span of interest may be from the beginning of the introduction of the sample to the "peak arrival time" where the measured transmembrane pressure differential saturates at the maximum differential pressure measurable by the pressure sensors 206 and 207, or the beginning of the introduction of the sample to some predefined time offset thereafter, or some other suitable time interval.

At 413 it is checked whether or not a lower temperature limit of the workflow has been reached. If the lower temperature limit has been reached, then the workflow proceeds to 414. Otherwise, if the lower temperature limit has not been reached, the workflow returns to 409 and the oil sample temperature is decremented again and 410 to 412 are repeated to generate additional transmembrane pressure differential data over time at the respective decremented temperature.

Once the lower temperature limit has been reached, in 414, the changes in transmembrane pressure differential over time as calculated in 412 during each temperature iteration of 409 to 412 are analyzed to determine the presence of wax in the oil sample. If waxes are present in the oil sample, when the oil temperature is at or below the wax appearance temperature (WAT), it is expected that the higher molecular weight wax will crystallize and form solid particles that will be collected by the microfluidic membrane filter 303a, thereby raising the transmembrane pressure differential over time. However, even if waxes are present in the oil sample, if the oil temperature is above the WAT, the transmembrane pressure differential over time will closely resemble the transmembrane pressure differential recorded during the fines determination in 401 to 408, as the only particles that might be retained by the membrane filter 303a are the fines.

If fines and waxes are both present in the oil sample, and the temperature of the sample is just below the WAT, then the transmembrane pressure differential will increase more quickly than if only fines were present, because in the former case there are two classes of solid matter blocking the membrane filter 303a instead of one class of solid matter in the latter case. Waxes and fines can also interact in a synergistic way that will result in rapid and substantial cake layer formation, as fines are known to be nucleation sites for wax crystallization. Therefore, whether waxes form with or without fines being present, the faster rate at which the membrane clogs and the steeper slope of the transmembrane pressure differential compared to those caused by fines will be indicative of the presence of waxes.

The analysis in 414 may include calculating an average slope of the transmembrane pressure differential over time for each respective temperature and analyzing those slopes as a function of temperature. The calculations of the slopes may indicate qualitatively whether or not the microfluidic membrane filter 303a is clogging at the respective temperatures. For example, a positive value of the average slope may indicate that over time, at the respective temperature, the transmembrane pressure differential was increasing, thereby indicating clogging of the membrane filter 303a. Also, if waxes form (as shown schematically in FIG. 6A) over the time span, then the slope of the transmembrane pressure differential over the time span would be expected to be greater than zero (i.e., a positive slope) and also greater (i.e., steeper) than the slope of the transmembrane pressure differential found during the fines determination in 401 to 408, as is shown in FIG. 6B.

If the microfluidic membrane filter 303a clogs, it is expected that the transmembrane pressure differential will saturate at the maximum differential pressure measurable by the pressure sensors 206 and 207. This condition occurs at the "peak arrival time" as referred to herein. In this case, the average slope of the transmembrane pressure differential for each temperature may be calculated as the average slope measured from a time at which the oil at the respective temperature is first injected into the microfluidic chip 111 to the peak arrival time. The analysis at 414 may further include plotting the calculated average slopes of the transmembrane pressure differential versus the respective temperatures to determine whether the slope data is positively or negatively correlated to temperature. In one embodiment, if it is determined that the slopes are negatively correlated to temperature (i.e., the slopes decrease with increasing temperature), then the analysis indicates that waxes are present in the oil sample. On the other hand, if it is determined that the slopes are not negatively correlated to temperature (i.e., the slopes do not increase with increasing temperature), then the analysis indicates that waxes are not present in the oil sample.

At 415 it is determined, based on the analysis in 414, whether or not wax is present in the oil sample. If the analysis indicates that wax is present, then the detection of waxes is set to 'true' at 417. Otherwise, if the analysis indicates that wax is not present, then the detection of waxes is set to 'false' at 416.

After 416 and 417 the workflow proceeds to the asphaltene detection portion of the workflow illustrated in FIG. 4B.

At 418, the temperature of the oil sample in the reservoir 103, along with the microfluidic chips 111 and 133, is set to the lower temperature limit of 413.

At 419, precipitant from reservoir 116 and/or solvent from reservoir 118 is introduced into the microfluidic chip 111 through inlet port 121 and mixed with the temperature-controlled oil sample at desired relative concentrations, and the mixture is flowed across the membrane filter 303a of the filtration chip 133 under applied pressure. The relative concentration of the precipitant can be configured to precipitate asphaltenes from the oil in the reactor section of the microfluidic chip 111 if such asphaltenes are present in the oil.

At 420, the pressure measurements of pressure sensors 206 and 207 are recorded over time while the mixture flows through the microfluidic chips 111 and 113.

At 421, changes in the transmembrane pressure differential over time (the pressure differential across the membrane filter 303a as recorded in 420 over time) are calculated. The time span of interest may be from the beginning of the introduction of the sample to the "peak arrival time" where the measured transmembrane pressure differential saturates at the maximum differential pressure measurable by the pressure sensors 206 and 207, or the beginning of the introduction of the sample to some predefined time offset thereafter, or some other suitable time interval.

At 421, the changes in the transmembrane pressure differential over time as calculated in 420 are analyzed to detect the presence of asphaltenes in the oil sample. For example, in one embodiment, the average slope of the transmembrane pressure differential over a time span between the introduction of the mixture to a peak arrival time may be calculated and compared to a predefined threshold, such as a value of zero to determine whether asphaltenes are present. That is, if the average slope of the transmembrane pressure differential over the time span is positive, that may be an indication that the microfluidic membrane filter 303a is being clogged due to the presence of asphaltenes in the oil sample that have been filtered by the membrane filter 303a.

At 422 it is determined whether the analysis in 421 indicates the presence of asphaltenes in the oil sample. If the analysis indicates the presence of asphaltenes in the oil sample, then the detection of asphaltenes is set to 'true' in 424. Otherwise, if the analysis does not indicate the presence of asphaltenes in the oil sample, then the detection of asphaltenes is set to 'false' in 423.

Figure 7B:
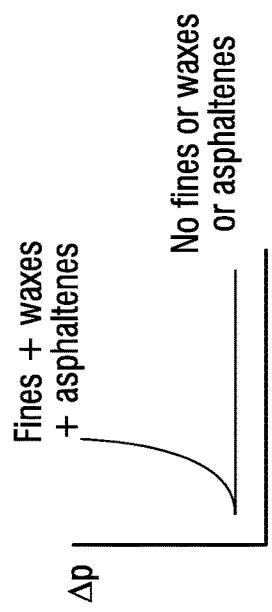
FIG. 7B is a graph showing transmembrane pressure differential as a function of time during asphantene formation.
Figure 7C:
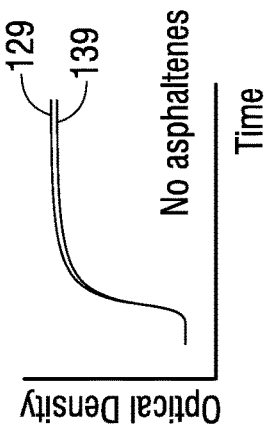
FIG. 7C is a graph showing optical densities as a function of time where no asphaltenes are present in the oil.
Figure 7D:
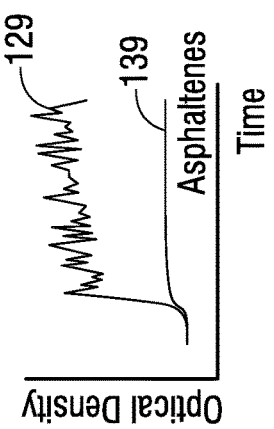
FIG. 7D is a graph showing optical densities as a function of time where asphaltenes are present in the oil.
Figure 7A:
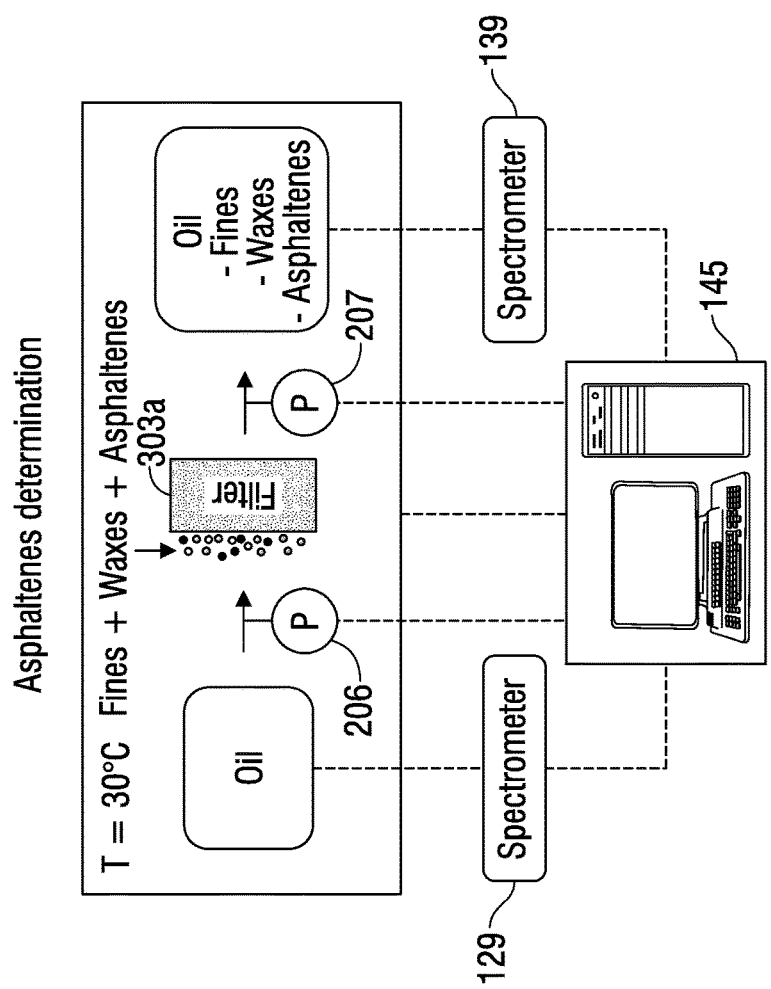
FIG. 7A is a schematic illustration of the automated test apparatus shown in FIG. 1 showing asphaltene formation.

The collection of asphaltenes by the membrane filter 303a may cause an increase in the measured transmembrane pressure differential over the time span during which the oil and precipitant are mixing, as shown in FIGS. 7A and 7B. As shown in FIG. 7B, when asphaltenes are precipitated, such as by the addition of a heptane precipitant to the oil sample, the asphaltenes collected by the membrane filter 303a cause the steepest transmembrane pressure differential response in comparison to those resulting from the collection of waxes and/or fines. Also, it will be appreciated from FIG. 7B that because the peak arrival time for the transmembrane pressure differential occurs much earlier when asphaltenes are precipitated than when waxes or fines are collected, the effects of wax formation and fines collection are essentially negligible in the asphaltene determination. Accordingly, the transmembrane pressure differential measurement can be used qualitatively to quickly verify the existence of asphaltenes in an oil sample without considering the effects of waxes and fines that may also be present in the oil sample.

FIG. 7C illustrates the optical densities of the oil measured by spectrometers 129 and 139 as a function of time where no asphaltenes are present in the oil. In this case the optical densities measured by the two spectrometers are essentially identical as, no asphaltenes being present, there are no asphaltenes for the membrane filter 303a to remove.

FIG. 7D illustrates the optical densities of the oil measured by spectrometers 129 and 139 as a function of time where asphaltenes are present in the oil. In this case the optical density measured by spectrometer 129 includes spikes due to light scattering from the asphaltene flocks on the inlet side of membrane filter 303a and is generally greater than the optical density of the filtered oil measured by spectrometer 139.

Also note that the apparatus 101 and associated workflow can use optical spectroscopy to characterize the asphaltenes of the oil sample. Examples of such optical spectroscopy techniques are described in U.S. Pat. No. 8,269,961 and PCT International Patent Application Publication Number WO 2013/126732 A1, both of which are incorporated herein by reference. For example, the apparatus 101 can be used to flow the oil at a temperature above the WAT so that the optical properties of the oil can be obtained using the spectrometers 129 and 139. Also, precipitant from reservoir 116 and/or solvent from reservoir 118 may be introduced into the microfluidic chip 111 through port 121 so that it is mixed with the flowing oil at desired relative concentrations to initiate precipitation of asphaltene flock if asphaltene is present. After the mixing with the precipitant and/or solvent, the optical properties of the mixture can be obtained using the spectrometers 129 and 139 for use in the analysis described in U.S. Pat. No. 8,269,961 and PCT International Patent Application Publication Number WO 2013/126732 A1. It should be noted that the optical technique used for quantification of asphaltene content can also be used to measure wax content of the oil by measuring the optical spectra and refractive index of the oil before and after wax collection by the membrane filter 303a and correlating the difference in the spectra to a concentration of wax.

Figure 5C:
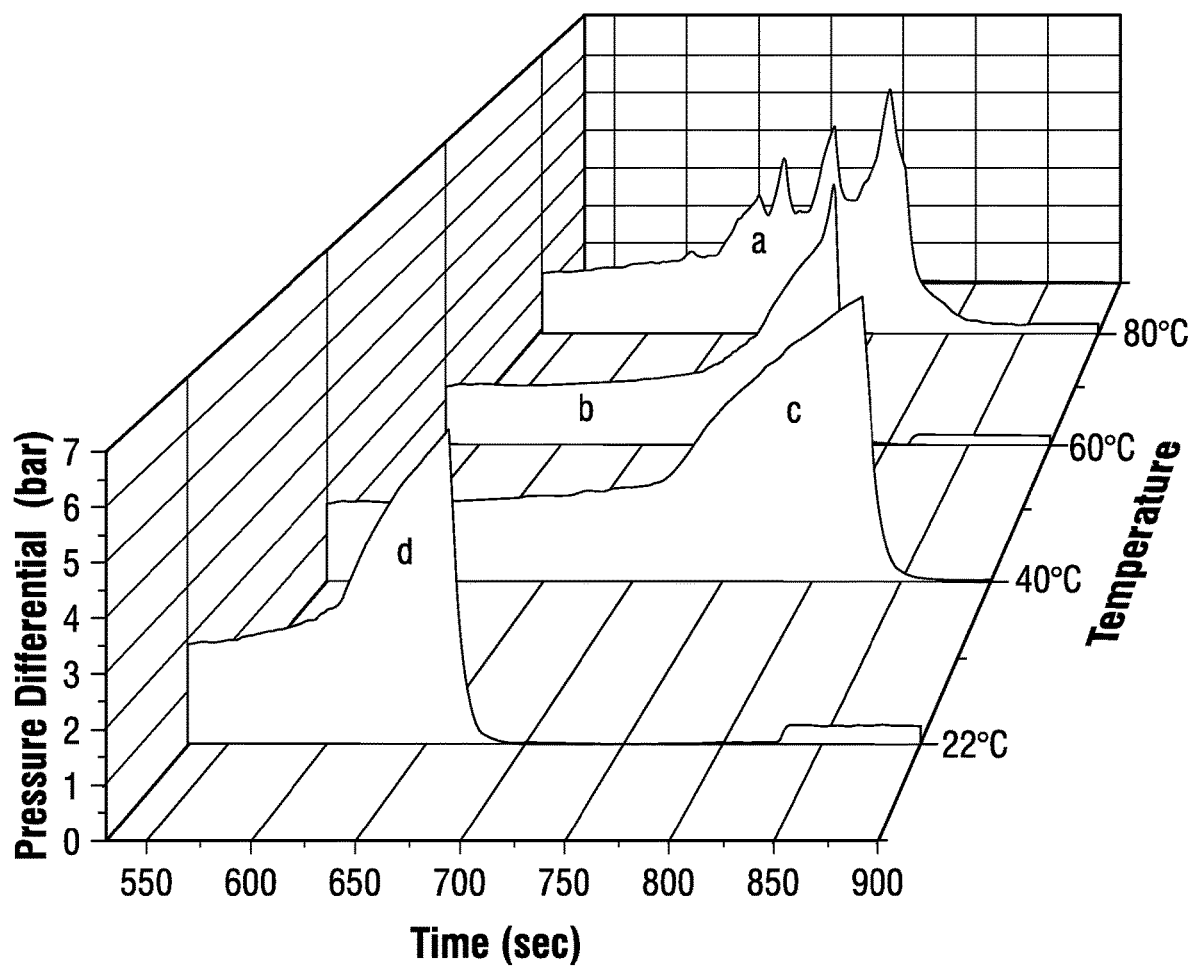
FIG. 5C is a graph of transmembrane pressure differential and temperature as a function of time for a sample with high fines content that is tested at various temperatures.

It should be noted that the presence of fines in an oil sample is generally independent of the temperature of the sample passing through the microfluidic chips 111 and 133, whereas the appearance of wax in an oil sample is dependent on the temperature of the sample passing through the microfluidic chips 111 and 133. For example FIG. 5C shows a waterfall plot for test runs of an oil sample with high fines content. The oil samples tested to obtain the data in FIG. 5C were all diluted 80:1 (toluene:oil) by mixing the oil from reservoir 103 with toluene from reservoir 118. This sample had a wax appearance temperature (WAT) of 35.2° C. (as measured by cross polarization microscopy (CPM)). One plot, labeled "a" in FIG. 5C, was obtained by performing 401 to 408 of the workflow of FIGS. 4A and 4B. At 401 the oil temperature was set by adjusting the temperature of the oil sample in the reservoir 103 and by setting the temperature of the temperature-controlled surface 150 above the WAT. In accordance with 403, the transmembrane pressure differential was recorded over an oil injection phase from 550 seconds to 900 seconds. The peak arrival time for plot "a" occurred at about 750 seconds. In accordance with 404, the change in transmembrane pressure differential over time was calculated. The change in transmembrane pressure differential over the oil injection phase was analyzed to determine the presence of fines in accordance with 405. Specifically, an average slope of the transmembrane pressure differential from 550 seconds to the peak arrival time was determined to be greater than zero, indicating the presence of fines at 406.

After the initial run for plot "a", the data for the remaining plots "b", "c", and "d" was generated by repeating 409 to 413 in the workflow of FIGS. 4A and 4B, each time decrementing the temperature of the oil sample to the temperatures shown in FIG. 5C. Regardless of temperature, the sample showed a rapid pressure differential build-up up to about 6 bar, which was the limit of the pressure sensors 206 and 207. The different peak shapes in FIG. 5C are attributed to sub-sampling variability and were also observed for repeat runs at the same temperatures. Although this oil sample tested in FIG. 5C had a wax appearance temperature (WAT) of 35.2° C. (as measured by cross polarization microscopy (CPM)), the fines content appeared to be higher than the wax content, thereby causing severe clogging early in the oil injection phase and at all temperatures tested in plots "a", "b", "c", and "d".

Also, as shown in FIG. 5C, at temperatures above the WAT (i.e., such as for plots "a", "b", and "c", the maximum transmembrane pressure differential of about 6 bar (the instrumentation limit) was reached between 750 and 850 seconds; whereas at temperatures below the WAT the maximum transmembrane pressure differential was reached earlier, i.e., at 650 seconds, indicating that when waxes crystallize from the oil, the waxes additionally contributed to the clogging by accelerating the clogging of the microfluidic membrane filter 303a relative to when waxes did not crystallize, i.e., remained liquefied. If the temperature is continually lowered further away from the WAT, more wax molecules with lower molecular weights can crystallize and form additional solid particles. Therefore, it is expected that as the temperature is lowered further below the WAT, the transmembrane pressure differential profile will show an earlier rise in transmembrane pressure differential as the pores of the membrane filter 303a clog more rapidly and flow is restricted sooner than when the temperature is closer to the WAT. In this way, observing the transmembrane pressure differential response to temperature change enables the presence of wax to be qualitatively determined and facilitates a quantitative determination of the WAT. If wax is not present, the slope of the transmembrane pressure differential response over time is not expected to change as temperature is varied. Moreover, because the collection of fines by the membrane filter 303a is independent of temperature variation, and the formation of wax is substantially related to temperature change, it is possible to determine wax formation as a function of temperature independently of the formation or presence of fines.

Figure 6C:
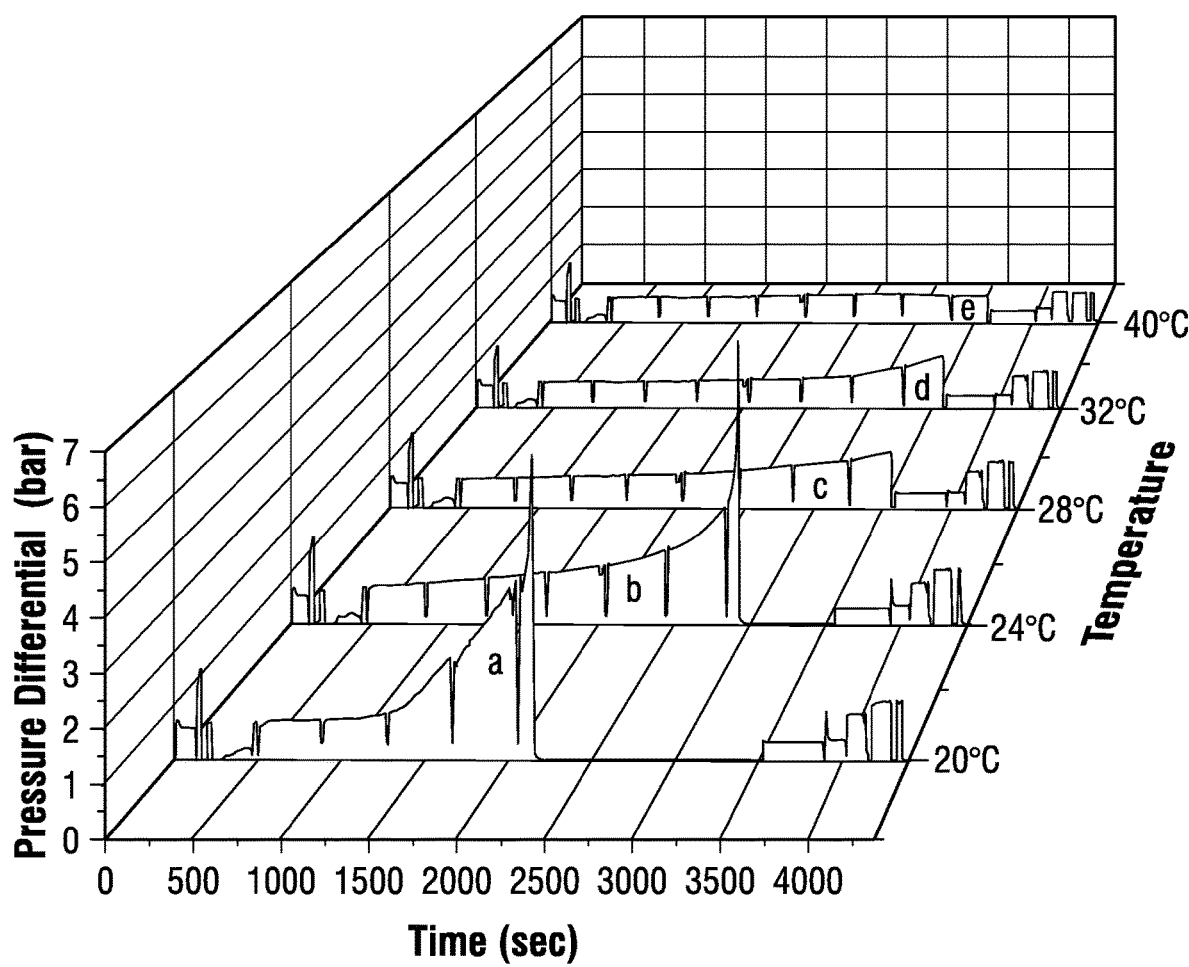
FIG. 6C is a graph of transmembrane pressure differential and temperature as a function of time for a sample that is tested at various temperatures and that contains waxes.

FIG. 6C shows a plot of transmembrane pressure differential and temperature as a function of time for a waxy crude oil sample diluted with toluene at a ratio of 80:1 (toluene:oil) while being run through the microfluidic chips 111 and 133 in accordance with 409 to 417 of the workflow of FIGS. 4A and 4B. The crude oil sample had a WAT of 32.2° C. (as measured by cross polarization microscopy (CPM)). The portion of interest of the graph is the oil injection phase occurring between 500 and 3500 seconds. The beginning pressure profile (between 0 and 500 seconds) and the ending pressure profiles (between 3500 and 4500 seconds) result, respectively, from priming and cleaning portions of an automated test protocol. Multiple iterations of the workflow 409 to 412 are performed, respectively, for crude oil sample temperatures of 20° C. (plot "a"), 24° C. (plot "b"), 28° C. (plot "c"), 32° C. (plot "d"), and 40° C. (plot "e"). When the crude oil temperature is at 40° C., there is no observable transmembrane pressure differential increase indicating that there is minimal clogging of the microfluidic membrane filter 303a and little to no fines content in the crude oil sample. It should be noted that within the oil injection phase, the periodic pressure drops were caused due to syringe refills and reloading of the crude oil sample in reservoir 103. However, when the crude oil temperature was decreased to 32° C. (i.e., slightly below the WAT), the transmembrane pressure differential started to rise after about 2500 seconds, indicating the presence of wax in the crude oil sample and indicating that the wax appearance temperature had been crossed. When 409 to 412 were repeated when the temperature of the crude oil was lowered from 32° C. to 28° C., more wax was deposited on the membrane filter 303a than at 32° C. and an earlier transmembrane pressure differential rise was noted starting at 2000 seconds. When 409 to 412 were repeated when the temperature of the crude oil was lowered from 28° C. to 24° C., enough wax solids formed to create a substantial transmembrane pressure differential increase that exceeded the instrumentation limit of 6 bar at around 3000 seconds and the system halted operation for flowing the crude oil sample from 3000 to 3500 seconds. Additionally, when 409 to 412 were repeated when the temperature of the crude oil was lowered from 24° C. to 20° C., the wax deposition occurred even more rapidly than when the temperature was at 28° C. and the pressure differential increase exceeded the instrumentation limit of 6 bar at approximately 2000 seconds and the system halted operation for flowing the crude oil sample from 2000 to 3500 seconds.

Figure 6D:
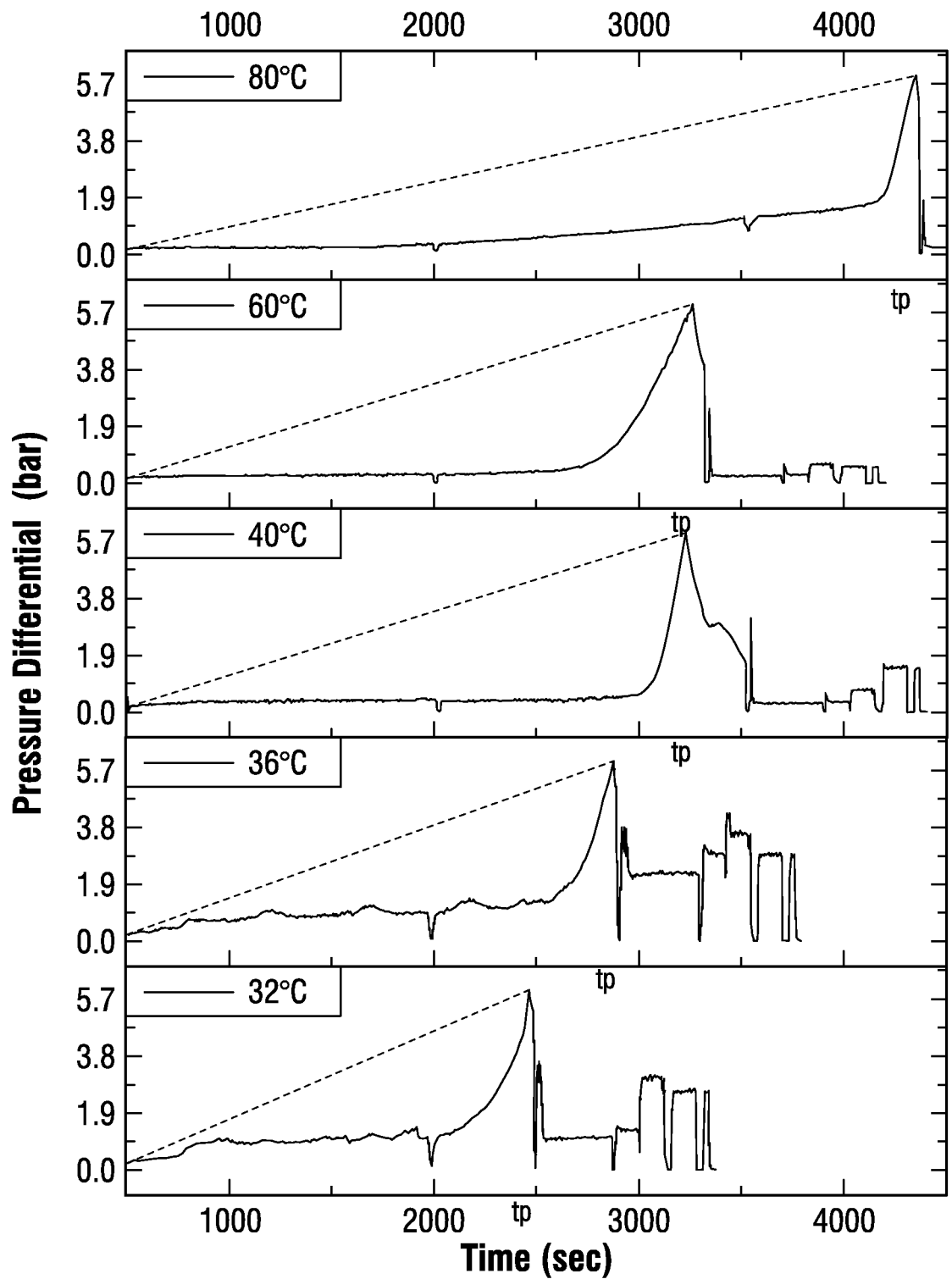
FIG. 6D illustrates transmembrane pressure differential data obtained for a stock tank oil sample that was tested at various temperatures.

An example of a calculation of a change in transmembrane pressure differential over time for a given temperature T will now be described with reference to FIG. 6D, which shows transmembrane pressure differential profiles for an oil sample tested in accordance with the workflow of FIGS. 4A and 4B. The priming portion of the plots from 0 to 500 seconds is not shown. The uppermost plot in FIG. 6D was obtained during the fines detection phase of the workflow from 401 to 408 when the oil sample was at a temperature above the WAT for the sample, while the other plots in FIG. 6D were obtained as a result of repeating 409 to 412 of the workflow of FIGS. 4A and 4B. At an oil temperature of 80° C. there was a gradual transmembrane pressure differential rise until a peak transmembrane pressure differential was reached at a peak arrival time ($t_p$) of about 4300 seconds or after about 630 µl of oil flowed through the membrane filter 303a. At oil temperatures of 60° C. and 40° C. there was a transmembrane pressure differential rise until the peak transmembrane pressure differential was reached at a peak arrival time ($t_p$) around 3250 seconds. At an oil temperature of 36° C. there was a transmembrane pressure differential rise until the peak transmembrane pressure differential was reached at a peak arrival time ($t_p$) around 2800 seconds. At an oil temperature of 32° C. there was a transmembrane pressure differential rise until the peak transmembrane pressure differential was reached at a peak arrival time ($t_p$) around 2500 seconds. For each plot in FIG. 6D, the average of the transmembrane pressure differential is shown as a straight dashed line from 500 seconds to the respective peak arrival time. As shown in FIG. 6D, the slopes of these straight dashed lines increase as the temperature decreases, because as the temperature is reduced from 80° C. to 32° C., the maximum transmembrane pressure differential occurs at earlier peak arrival times. In other words, as the temperature is reduced from 80° C. to 32° C. the clogging of the membrane filter 303*a* occurs more rapidly, indicating the co-filtration of wax solids along with fines.

Figure 6E:
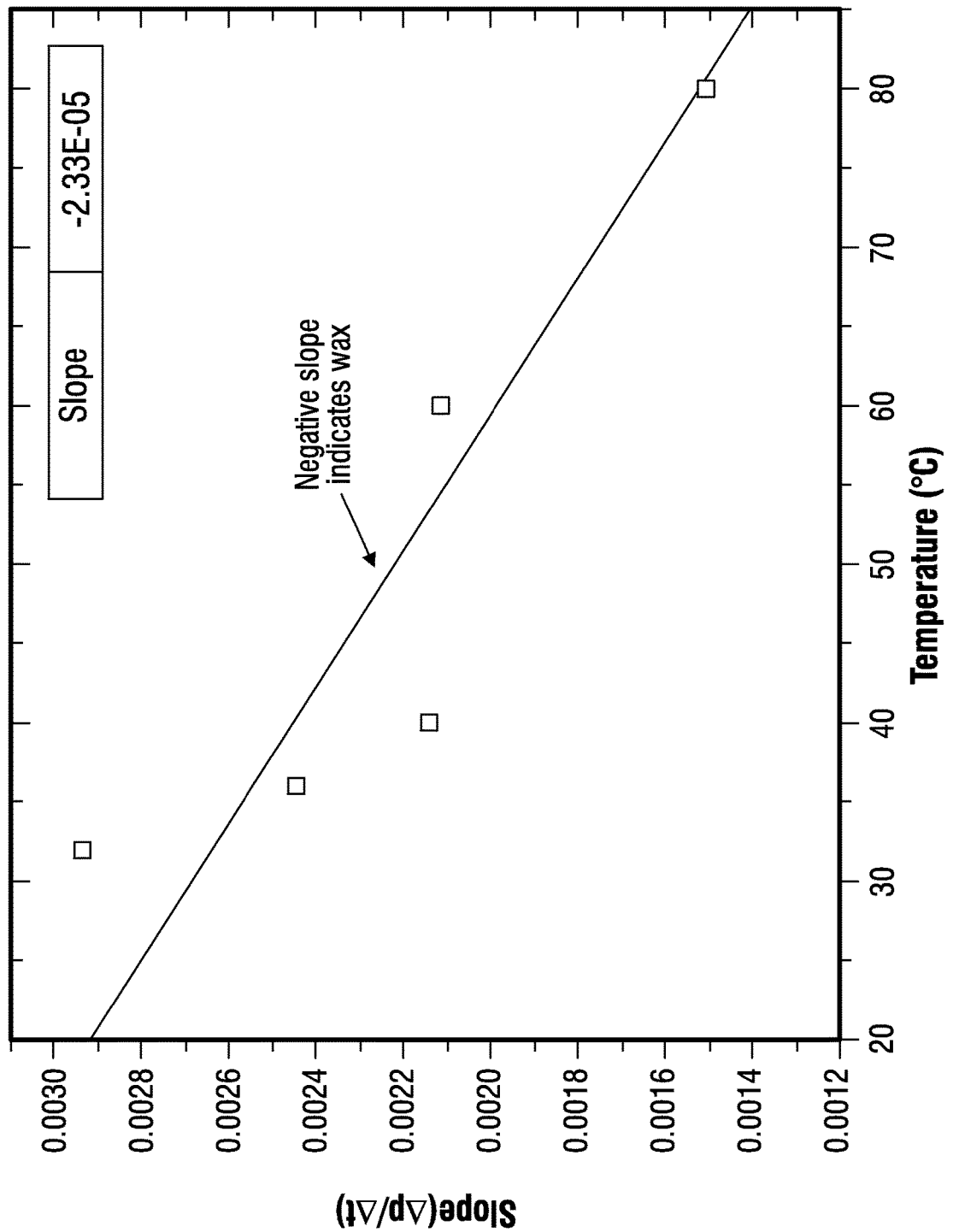
FIG. 6E is a plot of the slopes of the average transmembrane pressure differential curves shown in the graphs of FIG. 6D.

An example of the analysis of 414 of the workflow of FIGS. 4A and 4B will now be described with reference to FIG. 6E, which shows a plot of the slopes of the average transmembrane pressure differentials from FIG. 6D. The slopes are plotted against their respective temperatures. A linear regression line plotted in FIG. 6E for the slope data has a negative slope, indicating that as the temperature decreases, the average slope increases. In other words, the plots of FIGS. 6D and 6E indicate that the peak arrival time ($t_p$) occurs earlier (steeper slope) as temperature decreases, which is indicative of wax formation and, therefore, the presence of waxes in the oil sample. Therefore, a determination that the slope of the regression line in FIG. 6E is negative may be used in 414 in the workflow of FIGS. 4A and 4B to determine that wax is present in the oil sample and a determination that the slope of the regression line in FIG. 6E is not negative may be used in 414 in the workflow of FIGS. 4A and 4B to determine that wax is not present in the oil sample.

Owing to the microfluidic test apparatus and workflow described herein, a complete evaluation of an oil sample can be completed in hours as opposed to days, as is conventionally done. Detecting the presence of these solids in a rapid manner is important for making decisions with regard to flow assurance. For example, early detection of problematic waxes can identify that more in-depth investigations may be warranted, such as investigations using gas chromatography or other laboratory-based methods.

There have been described and illustrated herein several embodiments of a microfluidic test apparatus and methods of detecting fines, waxes, and asphaltenes in an oil sample. While particular embodiments of the invention have been described, it is not intended that the invention be limited thereto, as it is intended that the invention be as broad in scope as the art will allow and that the specification be read likewise. Thus, while particular microfluidic components have been disclosed, it will be appreciated that other components may be used as well. In addition, while particular types of precipitants and solvents have been disclosed, it will be understood that other suitable precipitants and solvents can be used. It will therefore be appreciated by those skilled in the art that yet other modifications could be made to the described apparatus and method without deviating from its scope as claimed.

What is claimed is:

1. A method for characterizing an oil, comprising:
   i) flowing at least one first sample containing the oil through a microfluidic device that has a microfluidic filter while controlling the temperature of the first sample flowing through the microfluidic device such that the temperature of the first sample is above wax appearance temperature for the oil;
   ii) in conjunction with i), using the microfluidic filter to perform microfluidic filtering operations that selectively block fines contained in the oil from passing through the microfluidic filter;
   iii) in conjunction with i) and ii), measuring and analyzing pressure difference across the microfluidic filter over time as the first sample is filtered in order to detect the presence of fines in the oil;
   iv) flowing at least one second sample containing the oil through the microfluidic device while controlling the temperature of the second sample flowing through the microfluidic device such that the temperature of the second sample is lower than wax appearance temperature for the oil;
   v) in conjunction with iv), using the microfluidic filter to perform microfluidic filtering operations that selectively block at least one of wax that crystallizes from the oil and fines contained in the oil from passing through the microfluidic filter; and
   vi) in conjunction with iv) and v), measuring and analyzing pressure difference across the microfluidic filter over time as the second sample is filtered in order to detect the presence of wax in the oil.

2. The method according to claim 1, further comprising:
   in conjunction with ii) and/or v), using a microfluidic mixer that is part of the microfluidic device to perform microfluidic mixing operations that mix a solvent with oil upstream of the microfluidic filter.

3. The method according to claim 1, wherein the operations of iv) involve iteratively decrementing the controlled temperature by a predetermined amount.

4. The method according to claim 2, wherein for a series of iterations, waxes are detected when a peak of the pressure difference measured and analyzed in vi) occurs earlier in time during each iteration as the temperature of the oil is iteratively decremented.

5. The method according to claim 1, wherein the detection of the presence of fines in the oil is based on the pressure difference measured in iii) as a function of time.

6. The method according to claim 5, wherein the detection of the presence of fines in the oil is based on a slope of the measured pressure difference.

7. The method according to claim 6, wherein:
   when the slope of the measured pressure difference is greater than a predefined threshold, the presence of fines in the oil is detected; and
   when the slope of the measured pressure difference is not greater than the predefined threshold, the presence of fines in the oil is not detected.

8. The method according to claim 1, further comprising:
   vii) flowing at least one third sample containing the oil through the microfluidic device while controlling the temperature of the third sample flowing through the microfluidic device such that the temperature of the third sample is below wax appearance temperature for the oil;
   viii) in conjunction with vii), using a microfluidic mixer that is part of the microfluidic device to perform microfluidic mixing operations that mix an asphaltene precipitant and/or solvent with the oil upstream of the microfluidic filter;
   ix) in conjunction with vii) and viii), using the microfluidic filter of the microfluidic device to perform microfluidic filtering operations that selectively block asphaltenes that precipitate from the mixture of viii) from passing through the microfluidic filter; and
   x) in conjunction with vii), viii), and ix), measuring properties of the mixture passing through the microfluidic filter in order to characterize asphaltenes in the oil.

9. The method according to claim 8, wherein the operations of x) involve measuring and analyzing pressure difference across the microfluidic filter over time as the mixture is filtered in order to detect the presence of asphaltenes in the oil.

10. The method according to claim 8, wherein the operations of x) involve performing optical spectroscopy on the mixture upstream of the microfluidic filter and performing optical spectroscopy on the filtered mixture downstream of the microfluidic filter, and using the results of such optical spectroscopy to quantify the concentration of asphaltenes in the oil.

11. The method according to claim 8, wherein the microfluidic processes are performed by at least one microfluidic chip.

12. A method according to claim 11, wherein:
the at least one microfluidic chip comprises first and second input ports that are fluidly coupled to a mixer section;
wherein the first input port is configured to supply the asphaltene precipitant and/or solvent to the mixer section for use in conjunction with the microfluidic mixing operations of viii); and
wherein the second input port is configured to supply the oil sample to the mixer section for use in conjunction with the microfluidic mixing operations of viii).

13. The method according to claim 12, wherein the at least one microfluidic chip comprises a reactor section fluidly coupled downstream from the mixer section.

14. The method according to claim 13, wherein the at least one microfluidic chip comprises a membrane filter section fluidly coupled downstream from the reactor section, wherein the membrane filter section includes the microfluidic filter.

15. The method according to claim 14, wherein the microfluidic filter has an average pore size of 200 nm or smaller.

* * * * *